United States Patent [19]

Okada et al.

[11] Patent Number: 4,759,827

[45] Date of Patent: Jul. 26, 1988

[54] OXYGEN CONCENTRATION DETECTION APPARATUS WITH AN ADJUSTING DEVICE AND ITS ADJUSTING METHOD

[75] Inventors: Yasushi Okada; Toyohei Nakajima; Toshiyuki Mieno; Nobuyuki Oono, all of Wako, Japan

[73] Assignee: Honda Giken Kogyo Kabushiki Kaisha, Tokyo, Japan

[21] Appl. No.: 934,590

[22] Filed: Nov. 25, 1986

[30] Foreign Application Priority Data

Nov. 29, 1985 [JP] Japan .................. 60-269094

[51] Int. Cl.$^4$ .................................... G01N 27/58
[52] U.S. Cl. ............................ 204/1 T; 204/406; 204/410; 204/412; 204/425; 204/427
[58] Field of Search .............. 204/406, 410, 412, 425, 204/426, 427, 1 S, 1 T

[56] References Cited

U.S. PATENT DOCUMENTS 4,505,806  3/1985  Yamada .................. 204/426
4,609,453  9/1986  Shimomura ............ 204/412
4,629,549 12/1986  Kojima ................... 204/412

Primary Examiner—John F. Niebling
Assistant Examiner—Ben C. Hsing
Attorney, Agent, or Firm—Pollock, VandeSande & Priddy

[57] ABSTRACT

An oxygen concentration detection apparatus includes a detection unit having a pair of oxygen-ion conductive solid electrolyte walls forming first and second gas retaining chambers on which first and second sets of electrodes, which are designed to operate alternatively, are provided. First and second current supply circuits are provided for alternatively supplying first and second pump currents respectively on the first and second sets of electrodes. Between the current supply circuits and the sets of electrodes respectively, a first variable resistor and a second variable resistor are provided so that adjustment operations are enabled separately for obtaining an accurate overall output signal characteristic of the oxygen concentration detection apparatus.

2 Claims, 5 Drawing Sheets

FIG. I

OXYGEN CONCENTRATION DETECTION APPARATUS WITH AN ADJUSTING DEVICE AND ITS ADJUSTING METHOD

BACKGROUND OF THE INVENTION

1. Field of the Invention

The present invention relates to an oxygen concentration detection apparatus with an adjusting device, and a method for adjusting the oxygen concentration detection apparatus.

2. Description of Background Information

In order to minimize the emissions of exhaust gas components and to improve the fuel economy of an internal combustion engine, a feedback type air/fuel ratio control system is generally used in which the oxygen concentration in the exhaust gas is detected and the air/fuel ratio of the mixture supplied to the engine is controlled to a target air/fuel ratio by a feedback control operation in accordance with a result of the detection of the oxygen concentration. As a type of oxygen concentration sensor for use in such a feedback type air/fuel ratio control system, there is an oxygen concentration sensor which generates an output signal varying generally in proportion to the change in the oxygen concentration in the gas whose oxygen concentration is to be measured. As an example, Japanese patent application laid open No. 52-72286 discloses a critical current type oxygen concentration detection device which includes a flat oxygen-ion conductive solid electrolyte member with a pair of electrodes on its main surface. The surface of one of the electrodes on the flat oxygen-ion conductive solid electrolyte member forms a part of a gas retaining chamber into which a gas whose oxygen concentration is to be measured (measuring gas) is introduced through an introduction orifice.

In this type of oxygen concentration detection device, the solid electrolyte member together with the pair of the electrodes operate as an oxygen pump unit. When a drive current is supplied between the electrodes so that the electrode located on the gas chamber's side operates as a negative electrode, oxygen in the gas filling the gas retaining chamber is ionized and migrates toward the surface of the electrode operative as a positive electrode. The oxygen ions are released through the surface of the positive electrodes in the form of the oxygen gas. The critical value of the current which can flow between the electrodes under this condition becomes substantially constant without regard to the change in the voltage of the supply current. On the other hand, it becomes proportional to the oxygen concentration in the measuring gas. Therefore, by detecting the magnitude of the critical current, the oxygen concentration in the measuring gas can be detected.

However, with the thus constructed oxygen concentration detection device, the output signal whose magnitude is proportional to the oxygen concentration is obtained only when the air/fuel ratio of mixture detected in terms of the oxygen concentration in the exhaust gas is on the lean side from the stoichiometric air/fuel ratio. Therefore, it was not possible to set a target air/fuel ratio value for the feedback air/fuel ratio control in a rich range of the air/fuel ratio.

There is another type of oxygen concentration detection device which can produce an output signal whose level is proportional to the oxygen concentraion in the exhaust gas both in the rich range and a lean range of the air/fuel ratio. As an example, there is a device which includes a pair of flat solid electrolyte members each of which are provided with a pair of electrodes. The surface of one of two electrodes provided on each solid electrolyte member respectively forms a part of the gas retaining chamber which in turn communicates with the measuring gas via an introduction orifice. The surface of the other electrode of one of the solid electrolyte members faces an atmospheric air chamber. This type of detection device is described in Japanese patent application laid open No. 59-192955.

In the case of this oxygen concentration detection device, one of the oxygen-ion conductive solid electrolyte members and its two electrodes are operative as the sensor cell unit for sensing the oxygen concentration, and the other one of the oxygen-ion conductive solid electrolyte members and its two electrodes are operative as an oxygen pump unit. With this construction, a drive current is supplied so that oxygen-ions in the oxygen pump unit move toward its electrode located on the gas retaining chamber's side when a voltage generated across the electrodes of the oxygen concentration detecting sensor cell unit is higher than a predetermined reference voltage. On the other hand, when the voltage across the electrodes of the sensor cell unit is lower than the predetermined reference voltage, the drive current is supplied so that the oxygen-ions move toward the electrode which is located on the opposite side from the gas retaining chamber. In this way, the variation of the current value becomes proportional to the oxygen concentration both in the lean range and the rich range of the air/fuel ratio.

However, in this type of oxygen concentration detection device having an output signal proportional to the oxygen concentration, its performance such as the signal output characteristic tends to vary from one product to the other through the manufacturing process of the oxygen concentration detection device which is made up of the oxygen pump unit and the sensor cell unit. In order to reduce such a variation, an increase of the production cost has been difficult to avoid. Otherwise, due to the deviation of the characteristic of the oxygen concentration detection device, the magnitude of the current supplied to the oxygen pump unit will vary from one product to the other with respect to the same value of the air/fuel ratio. Therefore, in such a case, it is difficult to detect the air/fuel ratio of the mixture accurately from the oxygen concentration in the exhaust gas.

SUMMARY OF THE INVENTION

An object of the present invention is therefore to provide an oxygen concentration detecting apparatus by which a uniform output characteristic can always be obtained irrespective of variation in the characteristic of the oxygen concentration detection unit.

Another object of the present invention is to provide a method for adjusting an oxygen concentration detection apparatus by which the deviation of the characteristic the oxygen concentration detection unit is readily compensated.

According to the present invention, an oxygen concentration detection apparatus includes a detection unit having a pair of walls made of an oxygen-ion conductive solid electrolyte arranged to form first and second gas retaining chambers, on which first and second sets of electrodes are provided. Pump currents are selectively supplied to electrodes of said first and second sets of electrodes via first and second variable resistances.

By suitably adjusting the resistance values of the first and second variable resistances, a desirable signal output characteristic is obtained over the rich and lean range of the air/fuel ratio.

In the method for adjusting the oxygen concentration detecting device according to the present invention, the current flowing across the electrodes of the oxygen pump unit is detected by means of a resistor, and the resistance of the resistor is determined in accordance with a characteristic curve of the variation of the voltage across terminals of the resistor obtained when the resistance value of the resistor is at a standard value.

DETAILED DESCRIPTION OF THE PREFERRED EMBODIMENT

Figure 1:
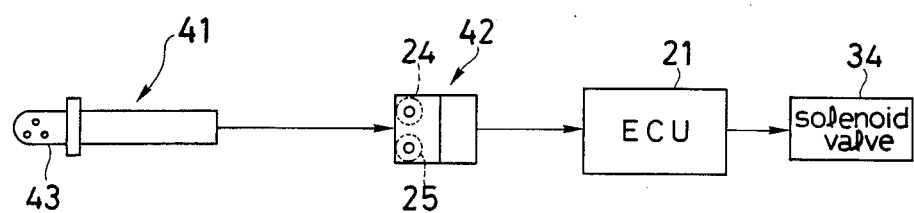
FIG. 1 is a diagram schematically illustrating an air/fuel ratio control system with an oxygen concentration detection apparatus of the present invention in which the adjusting method according to the present invention is applied.

Reference is first made to FIG. 1 showing the schematic diagram of an air/fuel ratio control system. The system includes an oxygen concentration detection device 41 which is to be positioned in an exhaust pipe of an internal combustion engine. Input/output signal lines of the oxygen concentration detection device 41 are connected to an electronic control unit (ECU) 21 via a connector 42. A pair of resistors 24 and 25 are provided in the connector 42.

Figure 2:
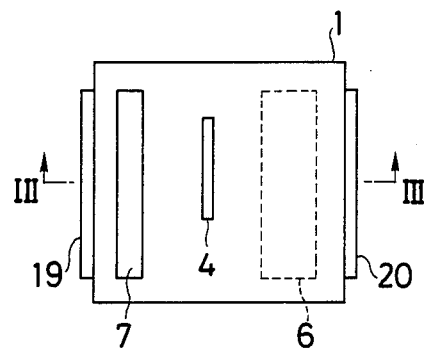
FIG. 2 is a plan view of the oxygen concentration detection unit used in the system shown in FIG. 1.
Figure 3:
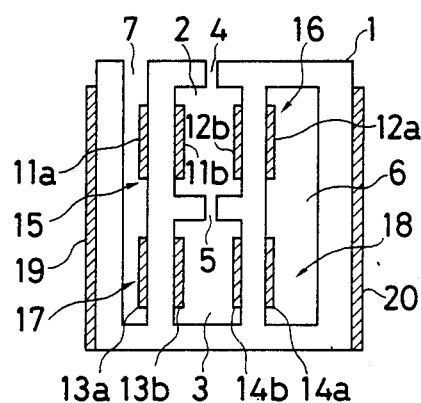
FIG. 3 is a sectional view of the oxygen concentration detection unit shown in FIG. 2, taken along a line III—III of FIG. 2.

The oxygen concentration detection device 41 has a protection case 43 in which an oxygen-ion conductive solid electrolyte member 1 having generally cubic configuration is provided as shown in the illustration of FIGS. 2 and 3. In the oxygen-ion conductive solid electrolyte member 1, first and second gas retaining chambers 2 and 3 which constitute gap portions are provided. The first gas retaining chamber 2 leads to a gas introduction port 4 for introducing the measuring gas, i.e. the exhaust gas of the engine, from outside of the oxygen-ion conductive solid electrolyte member 1. The gas introduction port 4 is positioned in an exhaust gas passage of the internal combustion engine so that the exhaust gas can easily flow into the first gas retaining chamber 2. In a wall between the first gas retaining chamber 2 and the second gas retaining chamber 3, there is provided a communication channel 5 so that the exhaust gas is introduced into the second gas retaining chamber 3 through the gas introduction port 4, the first gas retaining chamber 2 and the communication channel 5. Further, the oxygen-ion conductive solid electrolyte member 1 is provided with a reference gas chamber 6 into which outside air, for example, is introduced in such a manner that the reference gas chamber 6 is separated from the first and second gas retaining chambers 2 and 3 by means of a partition wall between them. In a side wall of the first and second gas retaining chambers 2 and 3, on the opposite side of the reference gas chamber 6, there is provided an electrode protection cavity 7. In the wall between the first gas retaining chamber 2 and the reference gas chamber 6 and the wall between the first gas retaining chamber 2 and the electrode protection cavity 7, there respectively are provided a pair of electrodes 12a and 12b, and a pair of electrodes 11a and 11b. The electrodes 11a, 11b, and 12a, 12b form a first set of electrodes associated with the first gas retaining chamber 2. Similarly, the wall between the second gas retaining chamber 3 and the gas reference chamber 6, and the wall between the second gas retaining chamber 3 and the electrode protection cavity 7 are respectively provided with a pair of electrodes 14a and 14b, and a pair of electrodes 13a and 13b. The electrodes 13a, 13b, and 14a, 14b form a second set of electrodes associated with the second gas retaining chamber 3. With this construction, the solid electrolyte member 1 and the pair of electrodes 11a and 11b together operate as a first oxygen pump unit 15. On the other hand, the solid electrolyte member 1 and the pair of electrodes 12a and 12b together operate as the first sensor cell unit 16. Similarly, the solid electrolyte member 1 and the pair of electrodes 13a and 13b together operate as a second oxygen pump unit 17, and the solid electrolyte member 1 and the pair of electrodes 14a and 14b together operate as the second sensor cell unit 18. Further, heater elements 19 and 20 are respectively provided on an outer wall of the reference gas chamber 6 and an outer wall of the electrode protection cavity 7, respectively. The heater elements 19 and 20 are electrically connected in parallel with each other so as to heat the first and second oxygen pump units 15 and 17, and the first and second sensor cell units 16 and 18 equally. The heater elements 19 and 20 further have an effect to enhance the heat retaining property of the solid electrolyte member 1. The solid electrolyte member 1 is made up of a plurality of pieces, to form an integral member. In addition, the walls of the first and second gas retaining chambers 2 and 3 need not be made of the oxygen-ion conductive solid electrolyte as a whole. At least portions of the wall on which the electrodes are provided must be made of the solid electrolyte.

As the oxygen-ion conductive solid electrolyte, zirconium dioxide ($ZrO_2$) is suitably used, and platinum (Pt) is used as the electrodes 11a through 14b.

Figure 4:
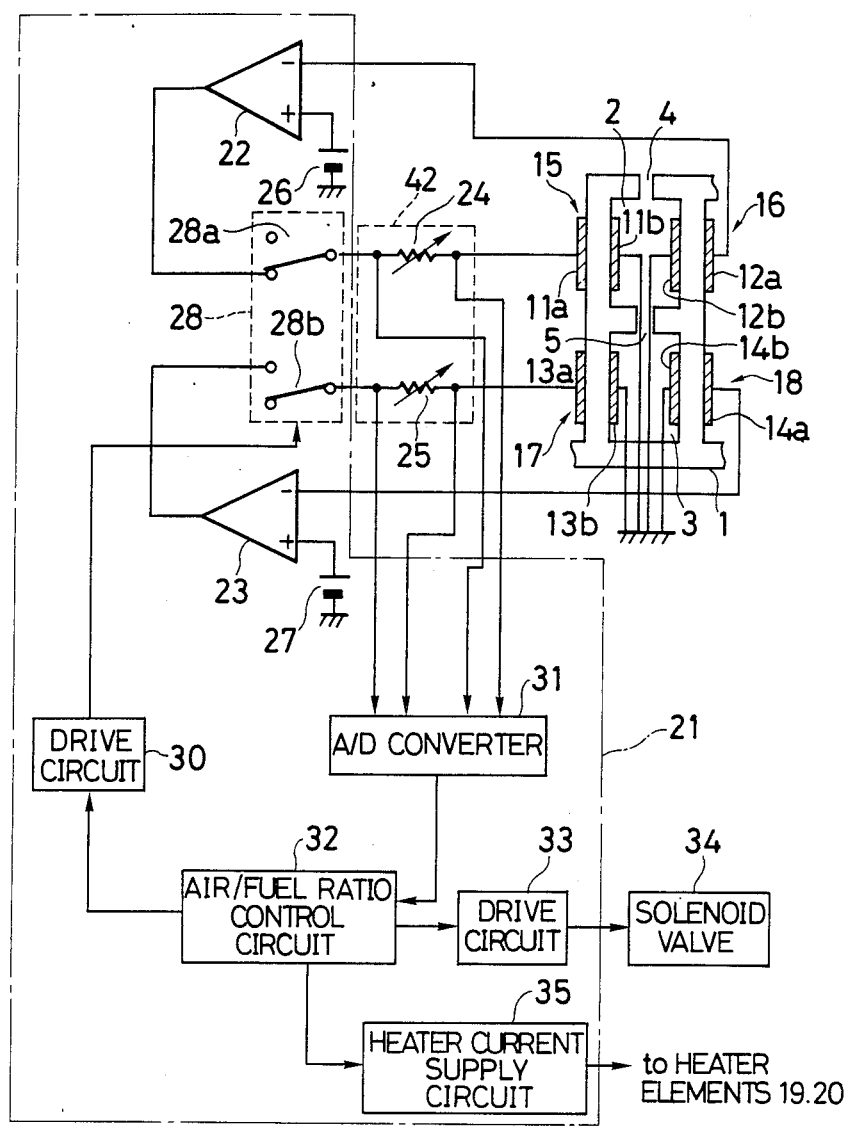
FIG. 4 is a circuit diagram of an electronic control system of the oxygen concentration detection apparatus according to the present invention.

As shown in FIG. 4, the ECU 21 includes differential amplifiers 22 and 23, variable resistors 24 and 25 for detecting the magnitude of the current, and sources of reference voltages 26 and 27, and a switch circuit 28. The electrode 11a provided on the outer surface of the first oxygen pump unit 15 is connected to an output terminal of the differential amplifier 22 through the variable resistor 24 provided in the connector 42 and a switch element 28a of the switch circuit 28. The electrode 11b provided on the inner surface of the first oxygen pump unit 15 is grounded. The electrode 12a provided on the outer surface of the first sensor cell unit 16 is connected to an inverting input terminal of the differential amplifier 22, and the electrode 12b on an inner surface of the first sensor cell unit 16 is grounded. Similarly, the electrode 13a provided on the outer surface of the second oxygen pump unit 17 is connected to an output terminal of the differential amplifier 23 through the variable resistor 25 in the connector 42, and a switch element 28b of the switch circuit 28. The electrode 13b provided on the inner surface of the second oxygen pump unit 17 is grounded. The electrode 14a provided on the outer surface of the second sensor cell unit 18 is connected to an inverting input terminal of the differential amplifier 23, and the electrode 14b provided on the outer surface of the sensor cell unit 18 is grounded. A non-inverting input terminal of the differential amplifier 22 is connected to the source of the reference voltage 26, and a non-inverting input terminal of the differential amplifier 23 is connected to the source of the reference voltage 27. Output voltages of the sources of the reference voltage 26 and 27 are set to a voltage (0.4 V for example) corresponding to the stoichiometric air/fuel ratio. With the circuit construction described above, the voltage appearing across the terminals of the variable resistor 24 forms an output signal of a first sensor, and the voltage appearing across the terminals of the variable resistor 25 forms an output signal of a second sensor. The voltages across the terminals of the variable resistors 24 and 25 are supplied to the air/fuel ratio control circuit 32 through the A/D converter 31 having a differential input circuit. Thus, pump currents $I_p$ (1) and $I_P$ (2) flowing through the variable resistors 24 and 25 are read by the air/fuel ratio control circuit 32. The air/fuel ratio control circuit 32 comprises a microcomputer. This air/fuel ratio control circuit 32 is supplied with output signals of a plurality of sensors (not shown) for sensing operational parameters of the engine, such as an engine rotational speed, an absolute pressure in the intake pipe, and a cooling water temperature. Further, the solenoid valve 34 is connected to the air/fuel ratio control circuit 32 via the drive circuit 33. The solenoid valve 34 is provided in an air intake side secondary air supply passage (also not shown) leading to an intake manifold at a position downstream of a throttle valve of a carburetor of the engine. The air/fuel ratio control circuit 32 further controls the switching operation of the switch circuit 28, in such a manner that the drive circuit 30 drives the switch circuit 28 in accordance with a command from the air/fuel ratio control circuit 32. In addition, the differential amplifiers 22 and 23 are supplied with positive and negative power voltages.

On the other hand, the heater elements 19 and 20 are supplied with currents from the heater current supply circuit so as to drive the heater elements 19 and 20 to heat the oxygen pump units 15 and 17, and the sensor cell units 16 and 18 to a suitable temperature level which is higher than the temperature of the exhaust gas.

With the thus constructed oxygen concentration detection apparatus, the exhaust gas in an exhaust manifold flows into the first gas retaining chamber 2 through the gas introduction port 4 and is diffused therein. Also, the exhaust gas entered in the first gas retaining chamber 2 is introduced into the second gas retaining chamber 3 through the communication channel 5 and is diffused therein.

In the switch circuit 28, when the switch element 28a is positioned to connect the output terminal of the differential amplifier 22 to the variable resistor 24 and the switch element 28b is positioned to open the line connecting the output terminal of the differential amplifier 23 and the variable resistor 25 open as shown in FIG. 4, the switch circuit 28 is in a condition for selecting the first sensor.

Under this condition for selecting the first sensor, the output signal level of the differential amplifier 22 is in a positive level when the air/fuel ratio of the mixture is in a lean range. This positive level output voltage is supplied to the series circuit of the first oxygen pump unit 15. Therefore, a pump current flows through the electrodes 11a and 11b of the first oxygen pump unit 15. Since this pump current flows from the electrode 11a to the electrode 11b, oxygen in the first gas retaining chamber 2 is ionized at the electrode 11b and moves through the oxygen pump unit 15 to the electrode 11a. At the electrode 11a, the oxygen is released in the form of oxygen gas. In this way, oxygen in the first gas retaining chamber 2 is pumped out.

By the pumping out of oxygen in the first gas retaining chamber 2, a difference in the oxygen concentration develops between the exhaust gas in the first gas retaining chamber 2 and a gas in the reference gas chamber 6. By this difference in the oxygen concentration, a voltage $V_s$ is generated across the electrodes 12a and 12b of the sensor cell unit 16, and in turn supplied to the inverting input terminal of the differential amplifier 22. Therefore, the voltage of the output signal of the differential amplifier 22 becomes proportional to the differential voltage between the voltage $V_s$ and a voltage $Vr_1$ of the output signal of the source of the reference voltage 26. Thus, the magnitude of the pump current becomes proportional to the oxygen concentration in the exhaust gas.

Figure 5:
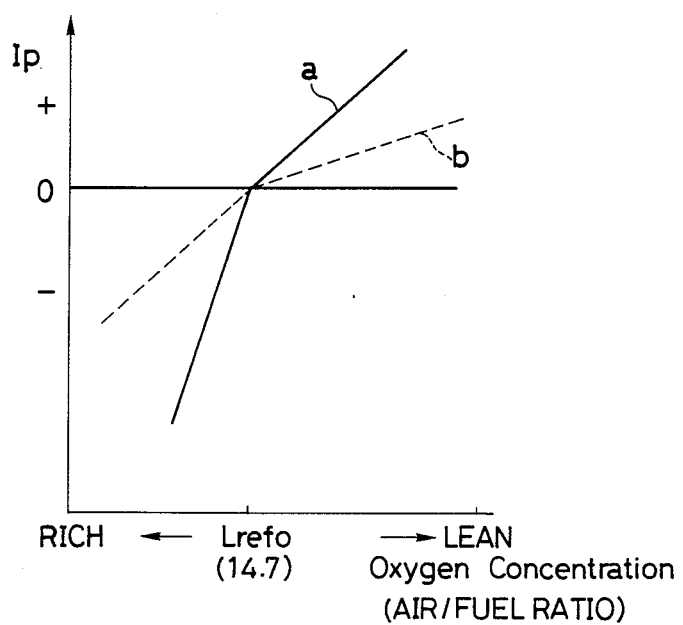
FIG. 5 is a diagram showing an output signal characteristic of the system shown in FIG. 1.

When the air/fuel ratio of the mixture is in a rich range, the voltage $V_s$ exceeds the output voltage $Vr_1$ of the source of the reference voltage 26. Therefore, the output signal level of the differential amplifier 22 turns from the positive level to the negative level. By this negative level, the pump current flowing across the electrodes 11a and 11b of the first oxygen pump unit 15 is reduced, and the direction of the flow of the current will be turned over. More specifically, the pump current will flow from the electrode 11b to the electrode 11a, so that the oxygen in the outside is ionized at the electrode 11a and in turn moves through the first oxygen pump unit 15 to the electrode 11b. At the electrode 11b, the oxygen is released in the form of oxygen gas into the first gas retaining chamber 2. In this way, the oxygen is pumped into the first gas retaining chamber 2. In summary, the operation of the apparatus is such that the pump current is supplied so that the oxygen concentration in the first gas retaining chamber 2 is maintained constant, and the oxygen is pumped in or out according to the direction of the pump current. Therefore, the magnitude of the pump current and the output signal voltage of the differential amplifier 22 become proportional to the oxygen concentration in the exhaust gas in both of the lean and rich ranges. In FIG. 5, the solid line shows the magnitude of the pump current $I_P$.

On the other hand, the pump current $I_P$ is expressed by the following equation:

$$IP = 4e\sigma_0 (Poexh - Pov) \qquad (1)$$

in which e represents the electric charge, $\sigma_0$ represents the diffusion coefficient of the gas introduction port 4 against the exhaust gas, Poexh represents the oxygen concentration of the exhaust gas, and Pov represents the oxygen concentration in the first gas retaining chamber 2.

The diffusion coefficient $\sigma_0$ can be expressed by the following equation:

$$\sigma_0 = D \cdot A / kTl \qquad (2)$$

where A represents the sectional area of the gas introduction port 4, k represents boltzmann's constant, T represents absolute temperature, l represents the length of the gas introduction port 4, and D represents a diffusion constant.

On the other hand, the second sensor unit is selected when the switch element 28a is positioned to open the line connecting the differential amplifier 22 and the variable resistor 24, and the switch element 28b is positioned to connect the differential amplifier 23 and the variable resistor 25.

In this state of selecting the second sensor unit, the pump current is supplied across the electrodes 13a and 13b of the second oxygen pump unit 17 so that the oxygen concentration in the second gas retaining chamber 3 is maintained constant by an operation the same as that in the state where the first sensor unit is selected. Thus, the oxygen is pumped in or out by the pump current and the magnitude of the pump current and the output signal of the differential amplifier 23 vary in proportion to the oxygen concentration both in the lean range and in the rich range.

In the state in which the second sensor unit is selected, the magnitude of the pump current can be expressed by using the equation (1) with the diffusion coefficient $\sigma_0$ calculated for the gas introduction port 4 and the communication channel 5, and the oxygen concentration in the second gas retaining chamber 3 as the value Pov.

On the other hand, it is known that the magnitude of the pump current becomes small as there is an increase in a diffusion resistance, which is inversely proportional to the diffusion coefficient, both in the lean range and the rich range of the air/fuel ratio. This means that, when the second sensor unit is selected, the diffusion resistance becomes larger than that in the state where the first sensor unit is selected. Therefore, as shown by the dashed line b in FIG. 5, the magnitude of the pump current is smaller than that in the state where the first sensor unit is selected, both in the lean range and in the rich range.

Further, by selecting suitable size and length of the communication channel 5, the characteristic curve of the pump current with the second sensor unit in the rich range connects at a straight angle to the characteristic curve of the pump current with the first sensor unit in the lean range, at a point where $I_P$ is zero ($I_P=0$). Thus, a characteristic curve of the pump current forming a straight line passing through the lean range and the rich range can be obtained by combining the first and second sensor units. Also, with suitable control operation, characteristic curves of the output signals of the first and second differential amplifiers 22 and 23 can be connected in a straight line to each other at a point where the voltage level is equal to zero.

In order to obtain the above mentioned continuous output characteristic, the air/fuel ratio control circuit 32 is designed to operate in the following manner.

Figure 6:
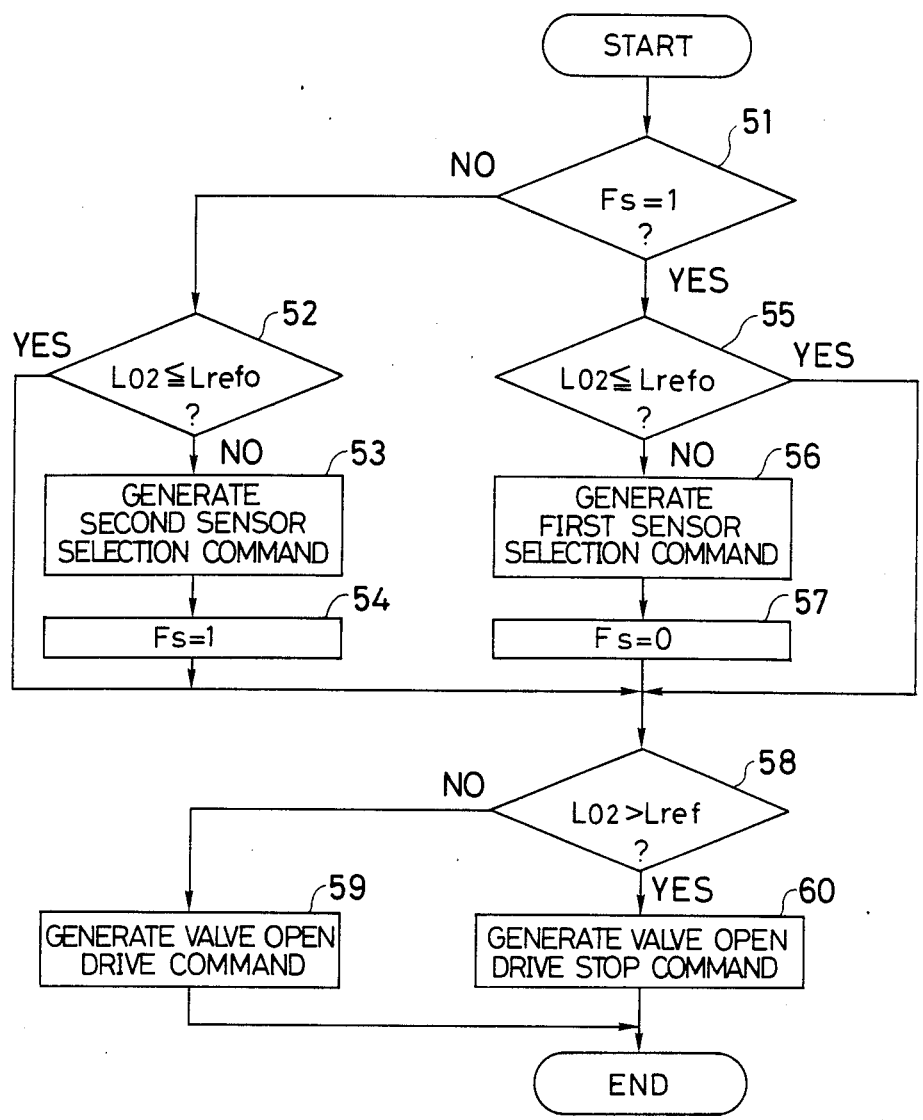
FIG. 6 is a flowchart showing the steps of the method for adjusting the oxygen concentration detection device according to the present invention.

As shown in FIG. 6, the air/fuel ratio control circuit 32 first detects whether or not a flag Fs indicative of the selection between the first and second sensor units is equal to "1" at a step 51. If Fs=0, it means that the first sensor unit is selected. Therefore, the control circuit 32 reads in a pump current value $I_P(1)$ of the first sensor unit from the A/D converter 31, and detects as to whether or not an oxygen concentration detection output signal value $L_{O2}$ corresponding to the pump current value $I_P(1)$ is higher than a reference value Lref0 which corresponds to a value 0V of an output signal $V_{S1}$ of the differential amplifier 22, at a step 52. If $L_{O2} \geq $ Lref0 ($V_{S1} \geq 0$), it means that the air/fuel ratio is in the lean range, and the selection of the first sensor unit is continued. If $L_{O2} <$ Lref0 ($V_{S1} < 0$), it means that the air/fuel ratio is in the rich range. In this state, a second sensor unit selection command is generated and supplied to the drive circuit at a step 53, and a value "1" is set for the flag Fs at a step 54. On the other hand, if Fs=1, it means that the second sensor unit is selected. Therefore, the control circuit 32 reads in a pump current value $I_P(2)$ of the second sensor unit from the A/D converter 31, and whether or not an oxygen concentration detection output value $L_{O2}$ corresponding to the pump current value IP (2) is lower than a reference value Lref0 corresponding to a value 0V of an output voltage $V_{S2}$ of the second differential amplifier 23, at a step 55. If $L_{O2} \leq $ Lref0 ($V_{S2} \leq 0$), it means that the air/fuel ratio is in the rich range, and the selection of the second sensor unit is continued. If, on the other hand, $L_{O2} >$ Lref0 ($V_{S2} > 0$), it means that the air/fuel ratio is in the lean range, and a first sensor unit selection command is generated and supplied to the drive circuit 30 at a step 56, and a value "0" is set for the flag Fs for indicating that the first sensor unit is selected at a step 57. In accordance with the first sensor unit selection command, the drive circuit 30 drives the switches 28a and 28b at the positions for selecting the first sensor unit as mentioned before, and this driving state is continued until the second sensor unit selection command is supplied from the air/fuel ratio control circuit 32. Also, in accordance with the second sensor selection command, the drive circuit 30 drives the switches 28a and 28b at the position for selecting the second sensor unit as mentioned before, and such a driving state is maintained until when the first sensor unit selection command is supplied from the air/fuel ratio control circuit 32. When the first sensor unit or the second sensor unit is selected in this way, the air/fuel ratio control circuit 32 detects whether or not the oxygen concentration detection output value of the first or second sensor unit output from the A/D converter 31 is greater than a target value Lref corresponding to the target air/fuel ratio at a step 58. If $L_{O2} \leq$ Lref, it means that the air/fuel ratio of the mixture is rich, and a valve open drive command for opening the solenoid valve 34 is generated and supplied to the drive circuit 33 at a step 59. If on the other hand, $L_{O2} >$ Lref, it mans that the air/fuel ratio of the mixture is lean, and the valve open drive stop command for closing the solenoid valve 34 is generated and supplied to the drive circuit 33 at a step 60. In accordance with the valve open drive command, the drive circuit 33 opens the solenoid valve 34 to introduce the secondary air into the intake manifold of the engine, so that the air/fuel ratio of the mixture is made lean. Conversely, in response to the valve open drive stop command, the drive circuit 33 closes the solenoid valve 34, so that the air/fuel ratio of mixture is enriched. By executing these operations repeatedly at predetermined intervals, the air/fuel ratio of the mixture supplied to the engine is controlled to the target air/fuel ratio. In the steps 52 and 55, the reference value Lref0, i.e. the reference voltage for the detection of $V_{S1}$ and $V_{S2}$, is set at 0V. However, it is also possible to set the reference voltage for detecting the voltage $V_{S1}$ at a level slightly lower than 0V, and to set the reference voltage for detecting the voltage $V_{S2}$ at a level slightly higher than 0V in order to provide a hysteresis characteristic.

The method for adjusting the oxygen concentration detection device according to the present invention will be further explained. In order to execute the adjustment, a testing machine which is capable of setting the air/fuel ratio of the mixture to be supplied to the engine at a desired value within a predetermined range of the air/fuel ratio will be used. In the adjusting procedure, the oxygen concentration detector 41 of the oxygen concentration detection apparatus is set in an exhaust pipe of the testing machine at first, and the resistance value of the variable resistors 24 and 25 are set at the standard value. Then, the air/fuel ratio of the testing machine is set at a predetermined value (18, for example) and pump current values of the first and second pump units 15 and 17, i.e the voltages across the terminals of the variable resistors 24 and 25 are measured. If the voltage appearing across the terminals of the variable resistor 24 differs from a voltage level derived from the output signal characteristic curve of the first sensor unit, using the predetermined value of the air/fuel ratio, an adjusting element of the variable resistor 24 is operated so that the voltage appearing across the terminals equals the derived voltage. In other words, by operating the adjusting element, a parallel shift of the output voltage characteristic curve of the variable resistor 24 occurs. Similarly, if the voltage appearing across the terminals of the variable resistor 25 differs from a voltage level derived from the output signal characteristic curve of the second sensor unit, using the predetermined value of the air/fuel ratio, an adjusting element of the variable resistor 25 is operated so that the voltage appearing across the terminals equals the derived voltage.

In the above explained embodiment of the present invention, the variable resistors 24 and 25 are used as resistors for detecting the pump current. However, this arrangement is not limitative, and fixed resistors prepared detachably, using a connector for example, can be used as the resistors for detecting the pump current.

In such a case, the air/fuel ratio is also set at a predetermined value, and whether or not the voltage across the terminals of the fixed resistor when a fixed resistor having a standard resistance value is used equals the voltage derived from the output signal characteristic of the sensor unit using the predetermined air/fuel ratio value is detected. If the voltage across the terminals of the fixed resistor differs from the derived voltage, the fixed resistor having the standard resistance value is replaced with another fixed resistor whose resistance value is experimentally determined, in accordance with the voltage difference. The adjustment of the output voltage characteristic is performed in this way.

It will be appreciated from the foregoing, according to the present invention, a pair of variable resistances are provided respectively between the first source of the pump current and the first oxygen pump unit, and between the second source of the pump current and the second oxygen pump unit which are operated alternatively. Thus, accurate adjustment operations are enabled for the variable resistances, so that a desirable overall output signal characteristic of the oxygen concentration detection apparatus is obtained.

According to the method for adjusting the oxygen concentration detection apparatus of the present invention, the resistance value of the resistor provided in the output circuit of the oxygen concentration sensing unit is adjusted in accordance with the voltage variation characteristic of the voltage appearing across the terminals of the resistor having the standard resistance value. Therefore, a uniform output characteristic can be obtained irrespectively of the deviation of the characteristic of the oxygen concentraion detection unit.

In this way, the accuracy of the detection of the oxygen concentration is improved and the air/fuel ratio of the mixture can be detected very accurately from the oxygen concentration in the exhaust gas. Moreover, the improvement can be realized at a low cost since the device is constructed such that the resistance value of a resistor for detecting the pump current which is connected in series with the oxygen pump element is varied for the adjusting operation.

What is claimed is:

1. An oxygen concentration detection apparatus, comprising:

an oxygen concentration detection device including a pair of walls made of an oxygen-ion conductive solid electrolyte and arranged to face each other so as to form first and second gas retaining chambers between them, first set of electrodes provided on inner and outer surfaces of each of said walls in a first portion forming said first gas retaining chamber so as to sandwich each of said walls, one of said walls being operative as an oxygen pump element and the other of said walls being operative as a sensor cell element, and second set of electrodes provided on inner and outer surfaces of each of said walls in a second portion forming said second gas retaining chamber so as to sandwich each of said walls, one of said walls being operative as an oxygen pump element and the other of said walls being operative as a sensor cell element; and first current supply means for supplying a first current across one pair of electrodes of said first set of electrodes, which are provided on said wall operative as the oxygen pump element, and controlling a magnitude of said first current so that a voltage generated across another pair of said first set of electrodes, which are provided on said wall operative as the sensor cell element, is maintained constant, whereby said magnitude of said first current represents a first detection value of said oxygen concentration;

second current supply means for supplying a second current across one pair of electrodes of said second set of electrodes, which are provided on said wall operative as the oxygen pump element, and controlling a magnitude of said second current so that a voltage generated across another pair of said second set of electrodes, which are provided on said wall operative as the sensor cell element, is maintained constant, whereby said magnitude of said second current represents a second detection value of said oxygen concentration;

switch control means for controlling a switch element connected between said first and second current supply means and said first and second sets of terminals, for enabling the supply of one of said first and second currents alternatively;

first variable resistance means connected between said first current supply means and said first set of electrodes; and second variable resitance means connected between said second current supply means and said second set of electroldes, whereby an adjustment of an overall output signal characteristic of the oxygen concentration detection apparatus is enabled.

2. A method of adjusting an oxygen concentration detection apparatus having a detection unit including a pair of walls made of an oxygen-ion conductive solid electrolyte and arranged to face each other so as to form first and second gas retaining chambers, and first and second sets of electrodes each set including two pairs of electrodes provided on inner and outer surfaces of each of said walls so as to sandwich each of said walls, one of said walls being operative as an oxygen pump element and the other of said walls being operative as a sensor cell element; and first and second current supply circuits for supplying, via first and second resistors, first and second pump currents across said two pairs of electrodes on said wall operative as the oxygen pump element, and controlling magnitude of said first and second pump currents so that voltages generated across said electrodes on said wall operative as the sensor cell element are maintained constnat respectively, and enabling the supply of one of said first and second pump currents alternatively, thereby obtaining an oxygen concentration detection output signal from magnitudes of said first and second pump currents in combination, the method comprising the step of:

varying each resistance value of said first and second resistors in accordance with respective voltages developing across terminals of each of said resistors, the resistance value of each of said resistors having been set at a standard value.

* * * * *